US009198824B2

(12) United States Patent
Scrase

(10) Patent No.: US 9,198,824 B2
(45) Date of Patent: Dec. 1, 2015

(54) STIMULATOR

(71) Applicant: Stephen Richard Scrase, Courtenay (CA)

(72) Inventor: Stephen Richard Scrase, Courtenay (CA)

(73) Assignee: G-LOVIN' ENTERPRISESS LLC, Wilmington, DE (US)

( * ) Notice: Subject to any disclaimer, the term of this patent is extended or adjusted under 35 U.S.C. 154(b) by 0 days.

(21) Appl. No.: 14/101,771

(22) Filed: Dec. 10, 2013

(65) Prior Publication Data

US 2015/0157529 A1 Jun. 11, 2015

(51) Int. Cl.

*A61B 17/20* (2006.01)
*A61M 37/00* (2006.01)
*A61H 23/00* (2006.01)

(52) U.S. Cl.

CPC .................................... *A61H 23/00* (2013.01)

(58) Field of Classification Search

CPC .......................................... A61H 19/00–19/50
USPC ........................................... 601/46, DIG. 16
See application file for complete search history.

(56) References Cited

U.S. PATENT DOCUMENTS

| | | | | |
|---|---|---|---|---|
| 2,548,004 | A * | 4/1951 | Duefrene | 24/662 |
| 3,461,859 | A * | 8/1969 | Fortnam | 601/74 |
| 6,203,509 | B1 * | 3/2001 | Duboff | 601/70 |
| 6,748,604 | B2 * | 6/2004 | Duboff et al. | 2/160 |
| 8,033,985 | B2 | 10/2011 | Smith | |
| 8,368,641 | B2 * | 2/2013 | Tremblay et al. | 345/156 |
| 2003/0181835 | A1 | 9/2003 | Klein | |
| 2009/0312599 | A1 | 12/2009 | Smith | |
| 2013/0261385 | A1 * | 10/2013 | Zipper | 600/38 |

FOREIGN PATENT DOCUMENTS

WO WO 2011/035339 * 3/2011

* cited by examiner

*Primary Examiner* — Kristen Matter

(57) ABSTRACT

A stimulator comprises a glove like member being configured to cover at least a portion of a user's hand. A bracket assembly is in engagement with the glove like member. The bracket assembly is configured to be disposed about one or more fingers of the user's hand. An extending part is configured to removably engage at least a palm side of the bracket assembly. A power pack is in engagement with the glove like member. The power pack is configured to communicate an amount of power to the extending part in engagement with the bracket assembly. A control assembly is configured to enable the user to control the communicated power in which contact of the extending part to a person's body part induces a stimulation.

19 Claims, 5 Drawing Sheets

STIMULATOR

CROSS-REFERENCE TO RELATED APPLICATIONS

Not applicable

RELATED CO-PENDING U.S. PATENT APPLICATIONS

Not applicable.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

FIELD OF THE INVENTION

One or more embodiments of the invention generally relate to personal massagers. More particularly, the invention relates to personal massagers which users may hold without gripping.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

In some instances, securing and/or operation of personal massagers may cause a number of undesirable conditions, including, without limitation, muscle fatigue, tendon and ligament strain, and pain. Some of these issues may be caused by an ergonomically dysfunctional design of the personal massagers.

The following is an example of a specific aspect in the prior art that, while expected to be helpful to further educate the reader as to additional aspects of the prior art, is not to be construed as limiting the present invention, or any embodiments thereof, to anything stated or implied therein or inferred thereupon. One such aspect of the prior art teaches of a sexual stimulation apparatus comprising a phallic-shaped member having a handle disposed at its base. By way of educational background, another aspect of the prior art generally useful to be aware of discloses a miniature sexual aid device embodied in a battery-powered electric vibrator which attaches to a user's finger. Another such aspect of the prior art teaches of a sexual stimulation apparatus comprising a phallic-shaped member having a handle disposed at its base. However, these solutions may not provide a device which may be effective while also providing a comfortable user experience. A solution which did so would be desirable.

In view of the foregoing, it is clear that these traditional techniques are not perfect and leave room for more optimal approaches.

BRIEF DESCRIPTION OF THE DRAWINGS

The present invention is illustrated by way of example, and not by way of limitation, in the figures of the accompanying drawings and in which like reference numerals refer to similar elements and in which.

Figure 1:
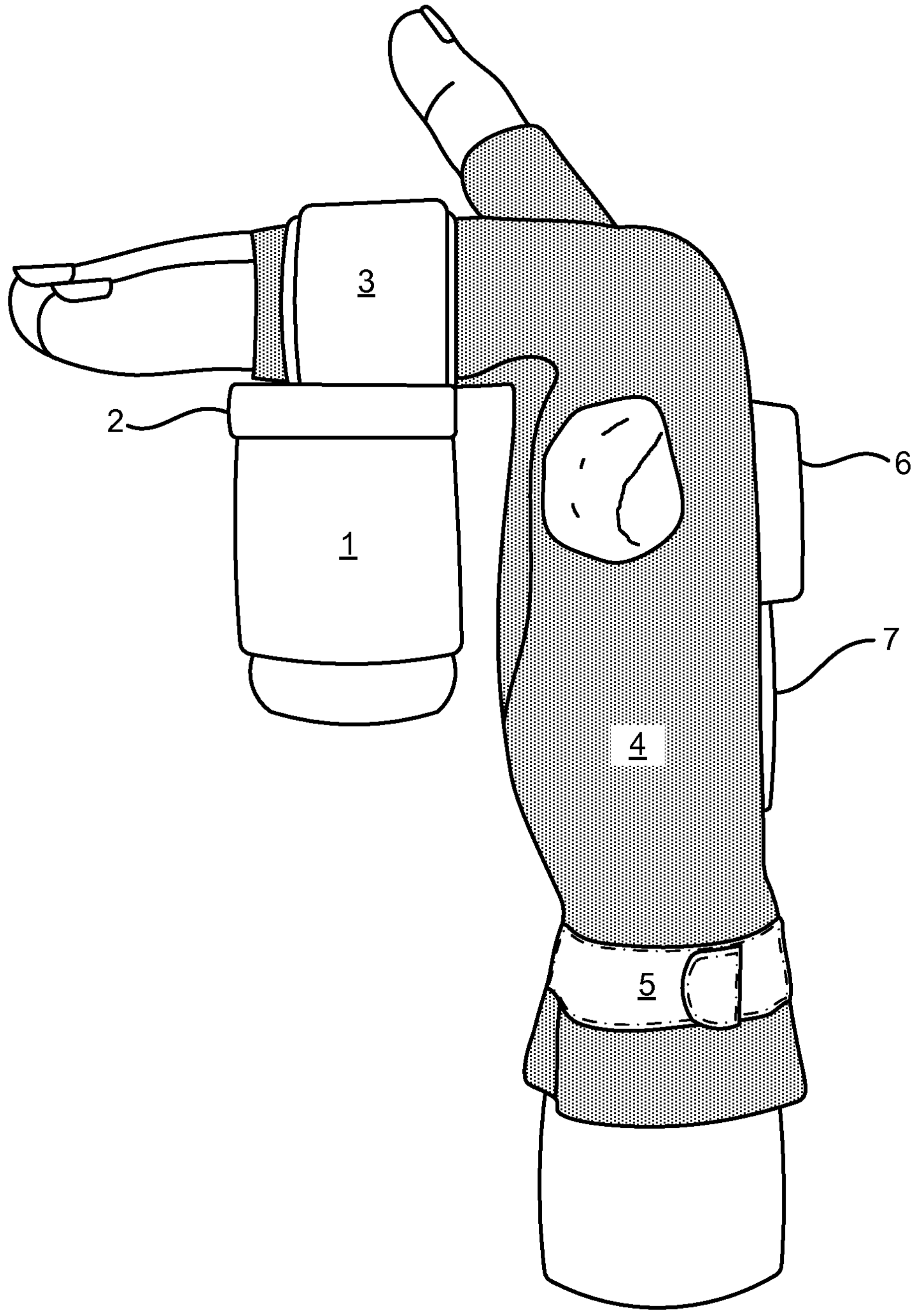
FIG. 1 is an illustration of an exemplary means for stimulation of body parts, in accordance with an embodiment of the present invention.

Unless otherwise indicated illustrations in the figures are not necessarily drawn to scale.

DETAILED DESCRIPTION OF SOME EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will now be described in detail with reference to embodiments thereof as illustrated in the accompanying drawings.

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

Headings provided herein are for convenience and are not to be taken as limiting the disclosure in any way.

The enumerated listing of items does not imply that any or all of the items are mutually exclusive, unless expressly specified otherwise.

The terms "a", "an" and "the" mean "one or more", unless expressly specified otherwise.

Devices or system modules that are in at least general communication with each other need not be in continuous communication with each other, unless expressly specified otherwise. In addition, devices or system modules that are in at least general communication with each other may communicate directly or indirectly through one or more intermediaries.

A description of an embodiment with several components in communication with each other does not imply that all such components are required. On the contrary a variety of optional components are described to illustrate the wide variety of possible embodiments of the present invention.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

In the following description and claims, the terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

It is to be understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

Some embodiments of the present invention may provide means and/or methods for stimulation, including, without limitation, sexual stimulation, of various parts of a body. Some of these embodiments may be suitable for a user's personal use.

FIG. 1 is an illustration of an exemplary means 100 for stimulation of body parts, in accordance with an embodiment of the present invention. In the present embodiment, an extending part 1 may extend from a bracket 3 which may be secured to one or more fingers. In some embodiments, one or more extending parts 1 may be composed of any suitable material, including, without limitation, medical grade silicon, and may be Phthalates-free, stainless steel, glass, plastic or Ceramic. In some of these embodiments, an internal structure of an extending part 1 may be composed of any suitable material, including, without limitation, ABS-type plastic. In many embodiments, a bracket 3 may be composed a mixture of one or more suitable materials, including, without limitation, metal and plastic. In some embodiments, a user may create motion in the extending part 1 through flexing and/or extension of the one or more fingers. In the present embodiment, the extending part 1 may extend from a palm side of a user's hand. In alternative embodiments, the extending part 1 may extend from a backside of a user's hand. In the present embodiment, the bracket 3 may connect to a glove 4. Further, in the present embodiment, the glove 4 may have a wrist strap 5 for securing the glove 4 in place. In some embodiments, a glove 4 may be composed of any suitable material, including, without limitation, neoprene, polyester, silicon, etc. Although in some embodiments the glove 4 may cover a large portion of a hand and/or wrist, in other embodiments the glove 4 may cover a smaller area and may be composed of less material.

Figure 2:
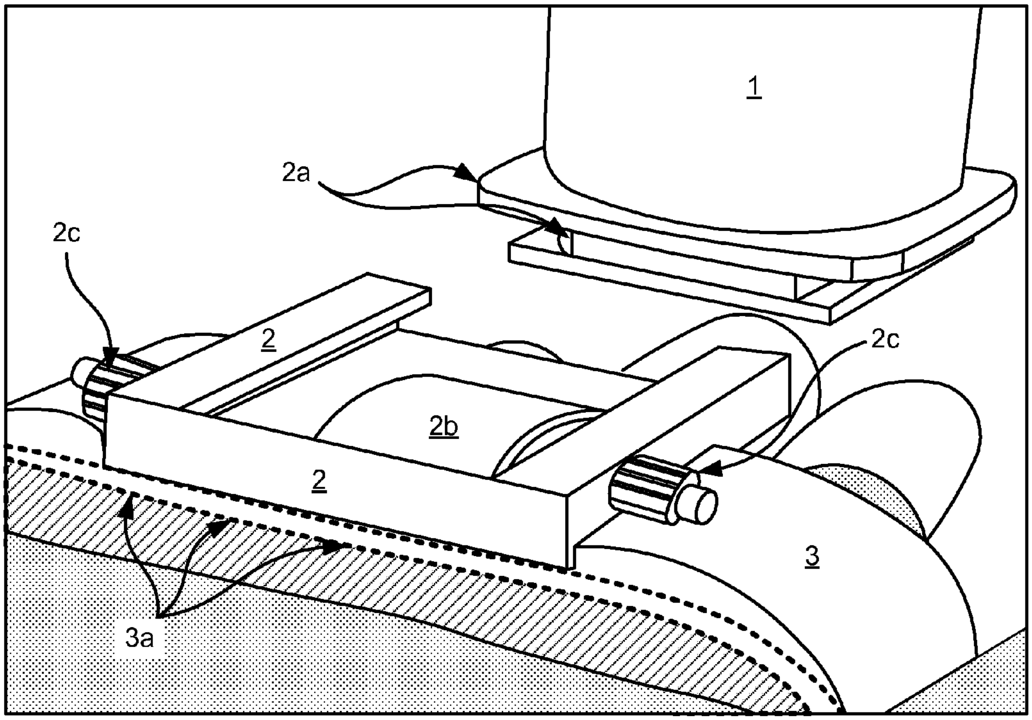
FIG. 2 is an illustration of an exemplary empty bracket 3, in accordance with an embodiment of the present invention.

FIG. 2 is an illustration of an exemplary bracket means 200, in accordance with an embodiment of the present invention. In the present embodiment, a bracket 3 may be suitable for securing an extending part 1 to a user's fingers. In some embodiments, a bracket 3 may be composed of any suitable material, including, without limitation, plastic. In the present embodiment, the bracket 3 may be attached to a glove 4. In some embodiments, a bracket 3 may attach to a glove 4 by means of stitching the bracket 3 to a bracket flange 3*a*. In the present embodiment, the bracket 3 may be positioned over a portion of the glove 4 which may cover one or more fingers. In a non-limiting example, a bracket 3 may be positioned over an index finger, a middle finger, and/or a $3^{rd}$ finger. In the present non-limiting example, the bracket 3 may be situated approximately 1.5 cm from a distal phalange of the middle finger. In many embodiments, a glove 4 may be any size to be suitable to fit varying sizes of hands.

In the present embodiment, an extending part 1 may have a base portion 2*a* which may fit into a base plate 2 portion of a bracket 3. Further, in the present embodiment, the base plate 2 may have a locking mechanism 2*c* for securing the base portion 2*a* in place. In some embodiments, the locking mechanism 2*c* may have one or more ends, or buttons, which users may engage to release the base portion 2*a*. In many embodiments, multiple types of extending parts 1 may be available, and users may switch out extending parts 1 using the locking mechanism 2*c* and ends, or buttons.

Further, in the present embodiment, a base plate 2 may house a conductivity point 2*b*. In some embodiments, a conductivity point 2*b* may allow transfer of power from a power source to the extending part 1. In some embodiments, the conductivity point 2*b* may be designed to make contact with a conduction plate which may be situated on a bottom side of the base portion 2*a*. In a non-limiting example, a conductivity point 2*b* may have a convex shape so as to extend outward and create contact with the base portion 2*a*. In the present non-limiting example, the conductivity point 2*b* may be composed of stainless steel or other suitable conductive material. In some embodiments, an extending part 1 may contain a motor. In some of these embodiments, a connection between the conductivity point 2*b* and a base portion 2*a* conduction plate may allow power, or electricity, to flow to the motor inside the extending part 1. In other embodiments, an extending part 1 may not contain a motor.

Figure 3:
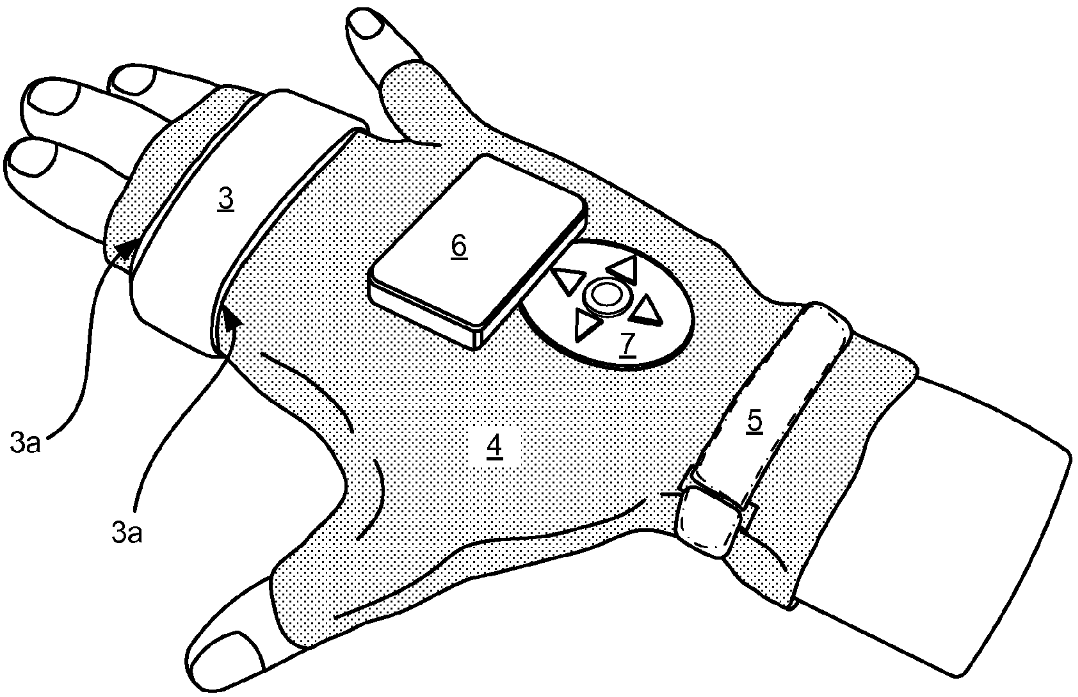
FIG. 3 is an illustration of a back side of an exemplary device, in accordance with an embodiment of the present invention.

FIG. 3 is an illustration of a backside of an exemplary device 300, in accordance with an embodiment of the present invention. In the present embodiment, a power pack 6 may store energy. In some embodiments, the power pack 6 may connect to system of wires. In the present embodiment, a system of wires may be embedded in the glove 4. In some embodiments, a system of wires may connect between the power pack 6 and the conductivity point 2*b*. In many embodiments, a power pack 6 may be a permanently affixed electromagnetic rechargeable battery which may be waterproof. In other embodiments, the power pack 6 may have a removable rechargeable battery. In still other embodiments, the power pack 6 may use disposable batteries.

In the present embodiment, motor controls 7 may transmit signals to the base plate 2. In some embodiments, the motor controls 7 may use a system of embedded wires to connect to the base plate 2. In other embodiments, a wireless system may be suitable for signal transmission. In the present embodiment, motor controls 7 may be positioned on a portion of the glove 4 which may be over a back of a user's hand, so as to provide easy access to the user. In alternative embodiments, motor controls 7 may extend a distance from the glove 4 to allow a user to perform controls using a different hand. In some of these embodiments, motor controls 7 may extend from the glove 4 by means of one or more wires and/or a wireless system. In many embodiments, motor controls 7 may determine a level of performance of a motor inside an extending part 1. In a non-limiting example, a parallel pin type connection point may connect motor controls 7 to a device motor. In the present non-limiting example, the connection point may be at a point in which the conductivity point 2*b* may contact a conduction plate of a base portion 2*a*. The control buttons allow for, but is not limited to, adjusting the mode of vibration, speed, on/off, electro-stimulation, thrusting, rotation and LED illumination of extending part 1. In some alternate embodiments, extending part 1 may be illuminated internally or externally. In some alternative embodiments, an extending part 1 may be suitable to extend further from a bracket 3 and retract to an original position. In some of these alternative embodiments, motor controls 7 may allow users to control extension of the extending part 1.

Figure 4:
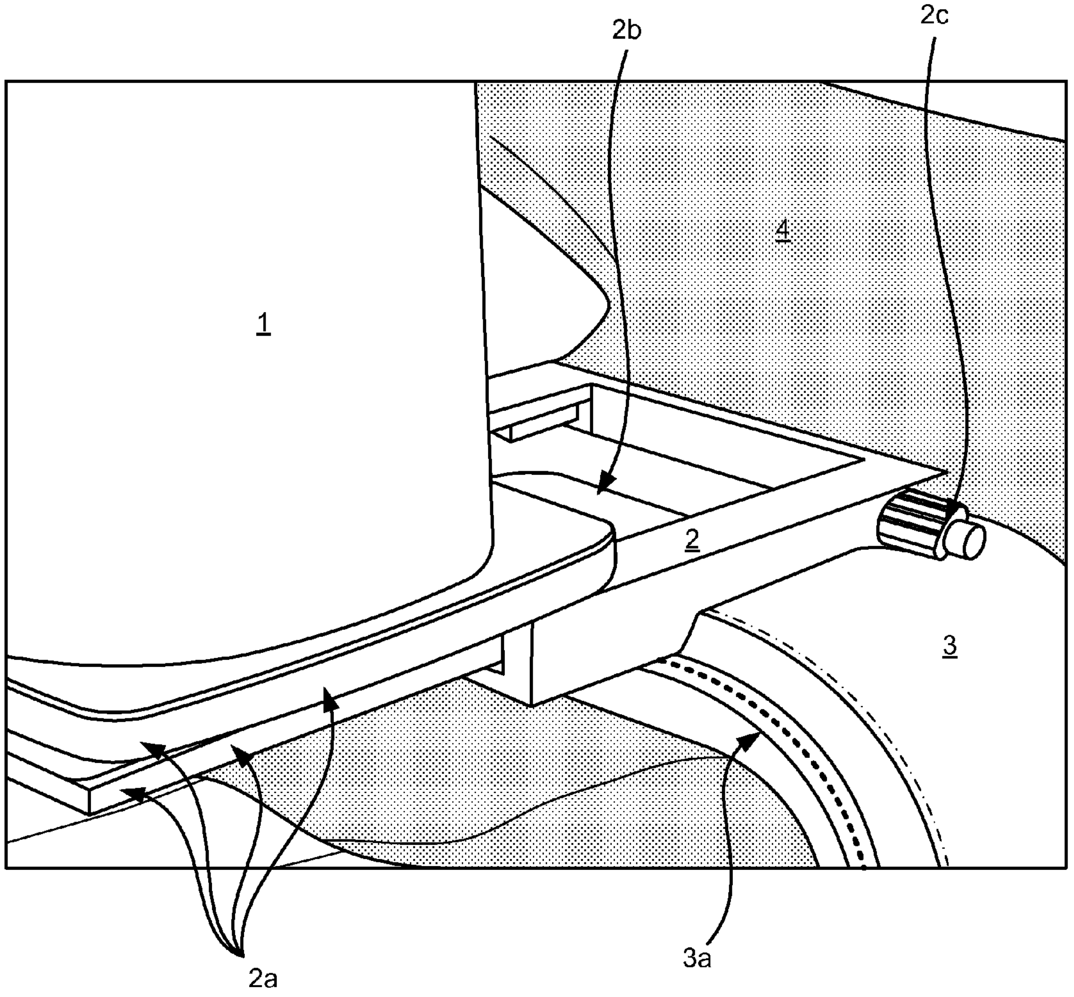
FIG. 4 is an illustration of interconnecting parts of a stimulation device, in accordance with an embodiment of the present invention.

FIG. 4 is an illustration of interconnecting parts of a stimulation device 400, in accordance with an embodiment of the present invention. In some embodiments, a base plate 2 may be any shape, including, without limitation, square, other rectangle, or circle/pin style. In the present embodiment, a base plate 2 may be a square and may have an upper lip which may fit over a bottom part of a base portion 2*a* and under a top part of a base portion 2*a*.

Figure 5:
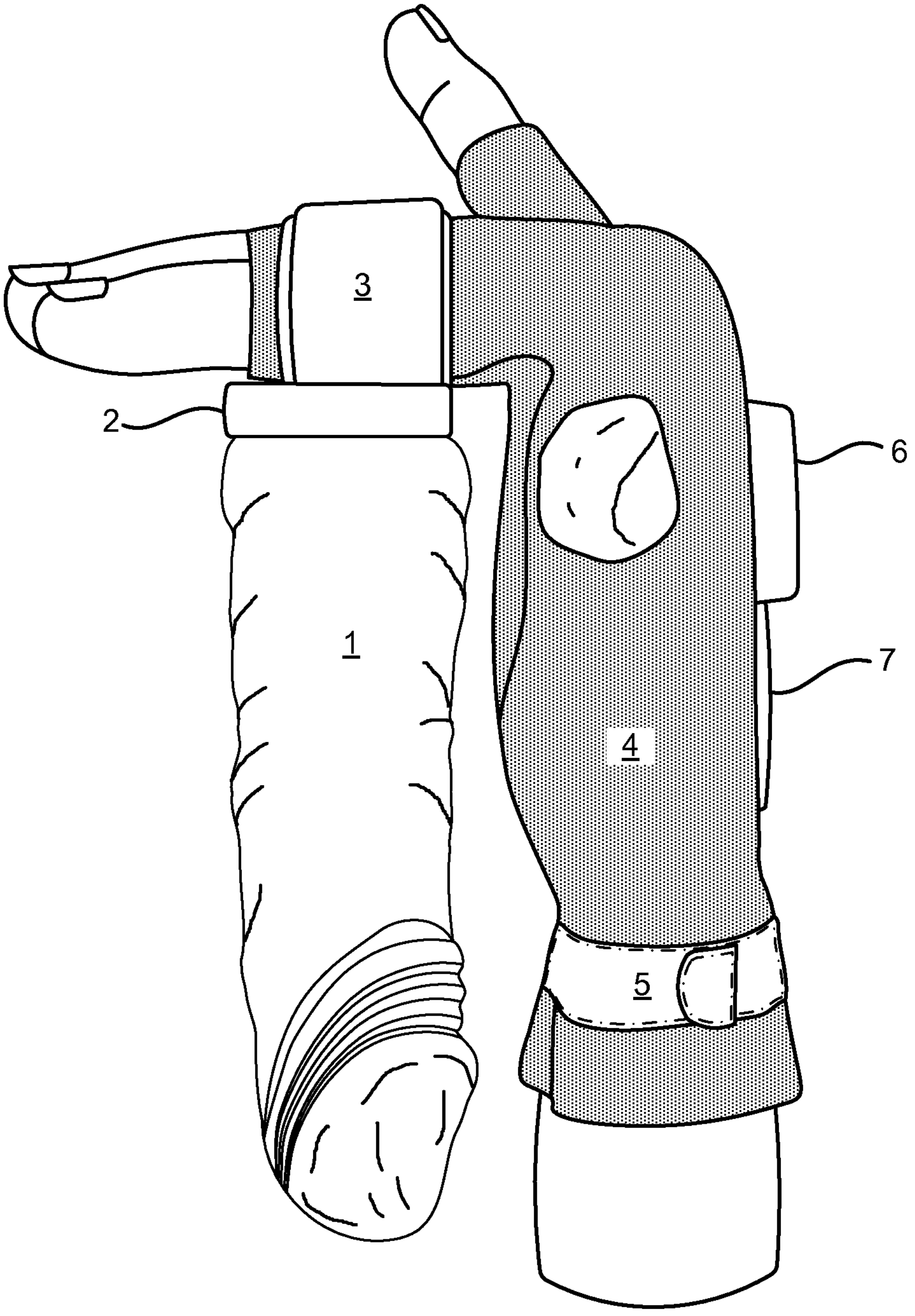
FIG. 5 is an illustration of an exemplary means for stimulation of body parts, in accordance with an embodiment of the present invention.

FIG. 5 is an illustration of an exemplary means 500 for stimulation of body parts, in accordance with an embodiment of the present invention. In some embodiments, extending part 1 may have a phallic shape. In some embodiments, one or more extending parts 1 may be composed of any suitable material, including, without limitation, medical grade silicon, and Phthalates-free plastic, stainless steel, glass, or ceramic. In some of these embodiments, an internal structure of an extending part 1 may be composed of any suitable material, including, without limitation, ABS-type plastic. In some embodiments, extending part 1 may comprise internal lighting such as, but limited to, LED lights which may be powered by power pack 6 and controlled by controls 7.

In some embodiments, various types of extending parts 1 may have variable specifications, including, without limitation, size, shape, texture, and motor functionality. In some embodiments in which an extending part 1 may have a motor, motorized variations may include without limitation, simple vibrational variations, assisted thrusting, LED light, and electronic stimulation.

In other embodiments, a glove 4 may comprise a small strip of material which may cover one or more fingers, and the small strip may extend to a user's wrist and form a wrap around the user's wrist. In some of these embodiments, a power pack 6 and motor control 7 may be situated on a section the glove 4.

In some embodiments, a bracket 3 may attach to one or more fingers without a glove 4. In some embodiments, bracket 3 may have a base plate 2 on the palm side of the bracket 3 and the on the backside of the bracket 3 to allowing for extending parts 1 to be utilized on either side or both sides simultaneously.

In other embodiments, a bracket 3 may be situated over a user's palm, and an extending part 1 may extend outwardly from the user's palm. In some of these embodiments, a user may create motion in the extending part 1 by flexing a wrist and/or arm.

In some embodiments, a bracket 3 may be circular in shape. In some of these embodiments, a round center pin may secure the bracket 3 to an extending part 1. Further, in some of these embodiments, the pin may slip into place and lock by means of a spring-loaded clip.

In many embodiments, an extending part 1 may be any of a variety of types, including, without limitation, dildos, vibrator nubs, bullet-type vibration massagers, "rabbit-type" vibrators/dildos, imitation vagina, etc.

In some embodiments, a connection point between motor and motor controls 7 may be any kind of connection, including, without limitation, fire wire, USB, or serial style.

In some embodiments, the bracket 3 may have the ability to adjust in order to fit the user's fingers more securely. This adjust may allow the bracket to be adjusted which may accommodate the different width and height of different users finger thickness when engaged in the bracket 3. In a non-limiting example, the adjustment may incorporate a sliding bar locking system where one piece of the bracket 3 may slide in or out of the bracket to allow for adjustment. When the desired "fit" is attained by user a lock pin mechanism may secure the bracket 3 in position. In the preceding example, the bracket 3 may be made out of, but not limited to, plastic, or a host of other rigid and semi rigid composites.

In some embodiments, the bracket 3 may also be used without the glove 4. In some embodiments, in order to position the bracket 3 in position, the bracket 3 may be secured to a full finger sleeve, with fingers fully encased, which may be slipped over the 3 fingers shown in FIG. 3 with the sleeve resting between the 3rd and pinky finger. The sleeve may be made of, but not limited to, a neoprene material. The Sleeve/bracket 3 may then be held in position by the pressure fit of the inserted fingers in the bracket 3. In some embodiments, a wrist strap may extend from the base of the sleeve over the back of the hand and then wrap around the wrist which pulls/holds the sleeve on the fingers when in operation.

In some embodiments, the bracket 3 may be designed like a pair of brass knuckles instead of a single oval bracket. This bracket embodiment may have individual rings attached to each other, which may then accommodate a finger in each. The base plate 2 may be attached to the bracket, which may then allow the various extending part 1 to be incorporated.

In some embodiments, the bracket 3 may be designed in such a way that it formed a rigid plastic casing. In a non-limiting example, the casing may extend from a proximal end of the fingers on the back of the hand over the finger tips to the proximal end of the fingers on the palm side of the hand. This arched finger bracket may secure a base plate 2 to allow for extending part 1 attachments to be used in the same manner as previously described. In some embodiments, the arched bracket may be secured using a wrist strap type holdfast so that while in operation the bracket may remain securely fastened in place over the fingers.

In an alternative embodiment of the device, the rigid bracket 3 may be replaced with a non-rigid, adjustable finger strap. The adjustable strap may allow the device to be secured to the operator's fingers using the 3-finger operation methodology. The finger strap may be made of, but not limited to, dense rubber composition, which may hold the base plate 2 on the palm side of the fingers. The finger strap may have "belt style" adjustment capabilities. This alternative embodiment may be used as a stand-alone with non-motorized or motorized attachments. In some embodiments, with motorized attachments, a remote power and control source may be attached via an arm band style holdfast which may use, but not limited to, a neoprene or other material as backing and hook and loop or any other type of method to secure to the arm. In some embodiments, the power/controls may be attached with a cord using any number of different electrical connections. The device may be operated by using the controls secured to the forearm. In alternate embodiments, a glove 4 may be incorporated in the same manner as the device show in FIG. 1 only without the finger portions protruding from the glove itself. In some embodiments, the "belt style" bracket may have direct contact with the fingers and power supply and motor controls may be fastened to the back of the hand.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

It is noted that according to USA law 35 USC §112 (1), all claims must be supported by sufficient disclosure in the present patent specification, and any material known to those skilled in the art need not be explicitly disclosed. However, 35 USC §112 (6) requires that structures corresponding to functional limitations interpreted under 35 USC §112 (6) must be explicitly disclosed in the patent specification. Moreover, the USPTO's Examination policy of initially treating and searching prior art under the broadest interpretation of a "mean for" claim limitation implies that the broadest initial search on 112 (6) functional limitation would have to be conducted to support a legally valid Examination on that USPTO policy for broadest interpretation of "mean for" claims. Accordingly, the USPTO will have discovered a multiplicity of prior art documents including disclosure of specific structures and elements which are suitable to act as corresponding structures to satisfy all functional limitations in the below claims that are interpreted under 35 USC §112 (6) when such corresponding structures are not explicitly disclosed in the foregoing patent specification. Therefore, for any invention element(s)/structure(s) corresponding to functional claim limitation(s), in the below claims interpreted under 35 USC §112 (6), which is/are not explicitly disclosed in the foregoing patent specification, yet do exist in the patent and/or non-patent documents found during the course of USPTO searching, Applicant(s) incorporate all such functionally corresponding structures and related enabling material herein by reference for the purpose of providing explicit structures that implement the functional means claimed. Applicant(s) request(s) that fact finders during any claims construction proceedings and/or examination of patent allowability properly identify and incorporate only the portions of each of these documents discovered during the broadest interpretation search of 35 USC §112 (6) limitation, which exist in at least one of the patent and/or non-patent documents found during the course of normal USPTO searching and or supplied to the USPTO during prosecution. Applicant(s) also incorporate by reference the bibliographic citation information to identify all such documents comprising functionally corresponding structures and related enabling material as listed in any PTO Form-892 or likewise any information disclosure statements (IDS) entered into the present patent application by the USPTO or Applicant(s) or any $3^{rd}$ parties. Applicant(s) also reserve its right to later amend the present application to explicitly include citations to such documents and/or explicitly include the functionally corresponding structures which were incorporate by reference above.

Thus, for any invention element(s)/structure(s) corresponding to functional claim limitation(s), in the below claims, that are interpreted under 35 USC §112 (6), which is/are not explicitly disclosed in the foregoing patent specification, Applicant(s) have explicitly prescribed which documents and material to include the otherwise missing disclosure, and have prescribed exactly which portions of such patent and/or non-patent documents should be incorporated by such reference for the purpose of satisfying the disclosure requirements of 35 USC §112 (6). Applicant(s) note that all the identified documents above which are incorporated by reference to satisfy 35 USC §112 (6) necessarily have a filing and/or publication date prior to that of the instant application, and thus are valid prior documents to incorporated by reference in the instant application.

Having fully described at least one embodiment of the present invention, other equivalent or alternative methods of implementing personal massagers according to the present invention will be apparent to those skilled in the art. Various aspects of the invention have been described above by way of illustration, and the specific embodiments disclosed are not intended to limit the invention to the particular forms disclosed. The particular implementation of the personal massagers may vary depending upon the particular context or application. By way of example, and not limitation, the personal massagers described in the foregoing were principally directed to sexual implementations; however, similar techniques may instead be applied to therapeutic uses, which implementations of the present invention are contemplated as within the scope of the present invention. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

Claim elements and steps herein may have been numbered and/or lettered solely as an aid in readability and understanding. Any such numbering and lettering in itself is not intended to and should not be taken to indicate the ordering of elements and/or steps in the claims.

The corresponding structures, materials, acts, and equivalents of all means or step plus function elements in the claims below are intended to include any structure, material, or act for performing the function in combination with other claimed elements as specifically claimed.

The Abstract is provided to comply with 37 C.F.R. Section 1.72(b) requiring an abstract that will allow the reader to ascertain the nature and gist of the technical disclosure. It is submitted with the understanding that it will not be used to limit or interpret the scope or meaning of the claims. The following claims are hereby incorporated into the detailed description, with each claim standing on its own as a separate embodiment.

What is claimed is:

1. A stimulator comprising:

a glove member, wherein said glove member being configured to cover at least a portion of a user's hand and wrist, and wherein said glove member is further configured to expose proximate distal ends of said user's fingers and thumb;

a bracket assembly, wherein said bracket assembly being in engagement with said glove member;

a flange, wherein said flange is configured to engage said bracket assembly to said glove member;

an extending part, wherein said extending part being configured to removably engage said bracket assembly, in which said extending part comprising a base portion being configured to fit into a base plate portion of said bracket assembly;

a base plate portion, in which said bracket assembly comprising said base plate portion, wherein said base plate portion is configured to generally accept said base portion of said extending part;

a power pack, wherein said power pack being in engagement with said glove member, in which said power pack being configured to communicate an amount of power to said extending part in engagement with said bracket assembly; and a control assembly, wherein said control assembly being configured to enable control of said communicated power.

2. The stimulator as recited in claim 1, in which said glove member further comprising a wrist strap being configured to secure said glove member approximately around said wrist portion of the user.

3. The stimulator as recited in claim 1, further comprising:

a locking mechanism, wherein said locking mechanism being configured to substantially secure said base portion in said base plate portion; and a button, wherein said button being configured to release said base portion from said base plate portion.

4. The stimulator as recited in claim 3, in which said extending part further comprising a motor configured to enable at least one of vibration, thrust and rotation of said extending part.

5. The stimulator as recited in claim 1, in which said power pack comprises a removable power pack, and in which said power pack further comprises a rechargeable battery pack.

6. The stimulator as recited in claim 5, in which said base portion of said extending part further comprises a conduction plate configured to receive said power.

7. The stimulator as recited in claim 6, in which said base portion is further configured to slidably engage with said base plate member.

8. The stimulator as recited in claim 6, in which said glove member further comprising a plurality of sizes being configured to fit different sizes of hands.

9. The stimulator as recited in claim 1, in which said bracket assembly further comprising a conductivity point for transferring the power to said extending part.

10. The stimulator as recited in claim 1, in which said extending part further comprises multiple extending parts, in which a locking mechanism and a button is configured to allow switching of said multiple extending parts.

11. The stimulator as recited in claim 1, in which said bracket assembly is further configured to be disposed proximately over at least one of an index finger, a middle finger and $3^{rd}$ finger of said user hand.

12. The stimulator as recited in claim 1, in which at least one of flexing and extension of one or more fingers of said user hand is operable to create a motion of said extending part.

13. The stimulator as recited in claim 1, in which said extending part further comprises an LED illuminator configured to illuminate in response to the controlled communicated power.

14. The stimulator as recited in claim 1, in which said control assembly is coupled to a proximate back side of said glove member, and in which said control assembly is configured to enable an adjustment of at least one of a vibration, speed, electro-simulation, thrusting and rotation of said extending part.

15. The stimulator as recited in claim 1, in which said extending part further comprises a phallic shaped member.

16. The stimulator as recited in claim 1, in which said glove member further comprises a neoprene material.

17. The stimulator as recited in claim 1, in which said extending part further comprises a phthalates-free material.

18. A stimulator comprising:

a glove member, wherein said glove member being configured to cover at least a portion of a user's hand and wrist, and wherein said glove member is further configured to expose proximate distal ends of the user's fingers and thumb;

a wrist strap, wherein said wrist strap being configured to secure said glove member approximately around said wrist portion of said user;

a bracket assembly, wherein said bracket assembly being in engagement with said glove member by stitching said bracket assembly to a flange;

an extending part, wherein said extending part being configured to removably engage said bracket assembly, in which said extending part being further configured to provide a response to a communicated amount of power;

a bracket assembly base plate portion, wherein said base plate portion is configured to generally accept said extending part;

an extending part base portion, wherein said base portion being configured to removably fit into said base plate portion;

a locking mechanism, wherein said locking mechanism being configured for securing said base portion of said extending part to said base plate portion of said bracket assembly;

a button, in which said button being configured to release said secured base portion, wherein said locking mechanism and button being operable to enable a user at least one of removal, replacement and switching of said extending part;

a power pack, wherein said power pack being coupled to a back side of said glove member, wherein said power pack being configured to communicate a controlled amount of power to said extending part in engagement with said bracket assembly;

a conductivity point, wherein said conductivity point being configured to transfer said controlled amount of power to said extending part;

a conduction plate, wherein said conduction plate being configured to receive said controlled amount of power; and a control assembly, wherein said control assembly being configured to control said transferred power, in which said control comprises an adjustment of at least one of vibration, speed, electro-simulation, thrusting and rotation of said extending part.

19. The stimulator as recited in claim 18, in which said extending part comprises a motor configured to perform said at least one of vibration, speed, electro-simulation, thrusting and rotation of said extending part in response to said controlled amount of power.

* * * * *